United States Patent
Dorner et al.

(10) Patent No.: US 8,637,002 B2
(45) Date of Patent: Jan. 28, 2014

(54) **NON-TOXIGENIC STRAINS OF *ASPERGILLUS FLAVUS* FOR CONTROL OF AFLATOXIN CONTAMINATION IN CROPS**

(75) Inventors: Joe W. Dorner, Albany, GA (US); Bruce W. Horn, Albany, GA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 65 days.

(21) Appl. No.: 13/009,430

(22) Filed: Jan. 19, 2011

(65) Prior Publication Data
US 2012/0183507 A1 Jul. 19, 2012

(51) Int. Cl.
*A01N 63/00* (2006.01)
*A01N 65/00* (2009.01)
*A01N 63/04* (2006.01)
*C12N 1/00* (2006.01)

(52) U.S. Cl.
USPC ..................................... 424/93.5; 435/256.1

(58) Field of Classification Search
None
See application file for complete search history.

(56) References Cited

U.S. PATENT DOCUMENTS

| | | | |
|---|---|---|---|
| 5,171,686 A | 12/1992 | Cotty | |
| 5,294,442 A | 3/1994 | Cotty | |
| 6,027,724 A | 2/2000 | Dorner et al. | |
| 6,306,386 B1 | 10/2001 | Cole et al. | |
| 2009/0060965 A1* | 3/2009 | Lyn et al. | ...................... 424/406 |

OTHER PUBLICATIONS

Chang et al. "Sequence breakpoints in the aflatoxin biosynthesis gene cluster and flanking regions in nonaflatoxigenic *Aspergillus flavus* isolates." Fungal Genetics and Biology 42 (2005) 914-923.*
Chang, P. et al.; "Sequence Breakpoints in the Aflatoxin Biosynthesis Gene Cluster and Flanking Regions in Nonaflatoxigenic *Aspergillus flavus* Isolates"; Fungal Genetics and Biology 42 (2005) 914-923.
Ehrlick, K.; "Effect on Aflatoxin Production of Competition Between Wild-type and Mutant Strains of *Aspergillus parasticus*"; Mycopathologia 97: 93-96 (1987).
Ehrlick, K.C. et al.; "An Isolate of *Apergillus flavus* Used to Reduce Aflatoxin Contamination in Cottonseed has a Defective Polyketide Synthase Gene"; Appl. Microbiol Biotechnol (2004) 65: 473-478.
Horn, B.W. et al.; "Soil Populations of *Aspergillus* Species from Section Flavi Along a Transect Through Peanut Growing Regions of the United States"; Mycologia, 90 (5), 1998, pp. 767-776.
Horn, B.W.; "Colonization of Wounded Peanut Seeds by Soil Fungi: Selectivity for Species from *Aspergillus* Section Flavi"; Mycologia, 97(1), 2005, pp. 202-217.
Horn, B.W. et al.; "Association of Morphology and Mycotoxin Production with Vegetative Compatibility Groups in *Aspergillus flavus*, *A. parastiticus*, and *A. tamarii*"; Mycologia, 88(4), 1996, pp. 574-587.
Horn, B.W. et al.; "Vegetative Compatibility within Populations of *Aspergillus flavus, A. parasiticus*, and *A. tamarii* from a Peanut Field"; Mycologia, 87(3), 1995, pp. 324-332.
Leslie, J.F.; "Fungal Vegetative Compatibility"; Annu. Rev. Phytopathol. 1993, 31: 127-50.
Mehl, H.L. et al.; "Variation in Competitive Ability Among Isolates of *Aspergillus flavus* from Different Vegetative Compatiblity Groups During Maize Infection"; Phytopathology, 100(2), 2010, 150-159.
Damann, K.E. et al.; "Biological Control of Aflatoxin Contamination Using Non-Toxigenic *Aspergillus flavus* "; Phytopatholosy 99:S27, (2009).
Cotty, P.J. et al.; "Competitive Exclusion of a Toxigenic Strain of *Aspergillus flavus* by an Atoxigenic Strain"; Postharvest Pathology and Mycotoxins, 83(12), 1993, 1283-1287.
Yu, J. et al.; "Clustered Pathway Genes in Aflatoxin Biosynthesis"; Applied and Environmental Microbiology, 2004, 1253-1262.
Wicklow, D.T. et al.; "Association Between Vegetative Compatibility and Aflatoxin Production by *Aspergillus* Species During Intraspecific Competition"; Mycoscience (2007), 48: 267-273.
Wicklow, D.T. et al.; "Effect of Intraspecific Competition by *Aspergillus flavus* on Aflatoxin Formation in Suspended Disc Culture"; Mycol. Res. 107(5), 2003, 617-623.
Cotty, P.J. et al.; "Variability Among Atoxigenic *Aspergillus flavus* Strains in Ability to Prevent Aflatoxin Contamination and Production of Aflatoxin Biosynthetic Pathway Enzymes"; Applied and Environmental Microbiology, 1994, 60(7), 2248-2251.

* cited by examiner

*Primary Examiner* — Blaine Lankford, Jr.
*Assistant Examiner* — Lauren K Van Buren
(74) *Attorney, Agent, or Firm* — John D. Fado; David L. Marks

(57) ABSTRACT

Non-toxigenic strains of *Aspergillus* are useful biocontrol agents for preventing toxin contamination in agricultural commodities, especially those for human consumption such as peanuts and corn, for example.

6 Claims, No Drawings

NON-TOXIGENIC STRAINS OF *ASPERGILLUS FLAVUS* FOR CONTROL OF AFLATOXIN CONTAMINATION IN CROPS

BACKGROUND OF THE INVENTION

1. Field of the Invention

This invention relates to novel strains of non-toxigenic *Aspergillus flavus* and compositions containing the strains and to methods for the preharvest control of *Aspergillus*-related toxins in crops.

2. Description of the Related Art

Aflatoxins produced by the fungi *Aspergillus flavus* and *Aspergillus parasiticus* are among the most carcinogenic compounds known from nature and are also acutely hepatotoxic in a variety of animals (Williams et al., American Journal of Clinical Nutrition, Volume 80, 1106-1122, 2004). These mycotoxins account for enormous monetary losses worldwide in crops such as, for example, peanuts, corn, tree nuts, spices, and cottonseed due to the costs associated with aflatoxin monitoring and the market rejection of crops (Robens and Cardwell, The Costs of Mycotoxin Management in the United States, in: *Aflatoxin and Food Safety*, ed. H. K. Abbas, Boca Raton, Fla.: CRC Press, 1-12, 2004). Regions of the world where aflatoxins are not regulated report periodic outbreaks of aflatoxicosis and associated human deaths (Krishnamachari et. al., Lancet, Volume 1, 1061-1063, 1975; Lye et al., American Journal of Tropical Medicine and Hygiene, Volume 53, 68-72, 1995, Azziz-Baumgartner et al., Environmental Health Perspectives, Volume 113, 1779-1783, 2005).

Aflatoxin contamination of peanuts, corn, and cottonseed can be effectively reduced through biological control measures in which large amounts of a non-toxigenic *A. flavus* strain are applied to fields (Dorner, Biological Control of Aflatoxin Crop Contamination, in: *Aflatoxin and Food Safety*, ed. H. K. Abbas, Boca Raton, Fla.: CRC. Press, 333-352, 2005). High populations of the applied non-toxigenic strain compete with native aflatoxigenic populations during crop invasion and thereby reduce aflatoxin contamination. Inoculum consisting of either conidia-coated or minimally colonized grain (Bock and Cotty, Biocontrol Science and Technology, Volume 9, 529-543, 1999; Dorner, Peanut Science, Volume 36, 60-67, 2009, Dorner et al., U.S. Pat. No. 6,306,386, issued Oct. 23, 2001; both herein incorporated by reference in their entirety) is applied during crop maturation to the soil surface where moisture absorption results in extensive sporulation and subsequent conidial dispersal of the non-toxigenic strain into soil and onto the plants. In corn, aerial application of inoculum onto developing ears appears to be more effective than the traditional method of soil application (Dorner, Journal of Food Protection, Volume 72, 801-804, 2009; Lyn et al., Food Additives and Contaminants, Volume 26, 381-387, 2009).

Two major non-toxigenic strains of *A. flavus* are currently registered through the United States Environmental Protection Agency for use in biological control of aflatoxins: AF36, which is approved for use on cotton (U.S. Environmental Protection Agency, 2003) and NRRL 21882, which is the active ingredient in AFLA-GUARD® for application to peanuts (U.S. Environmental Protection Agency, 2004) and whose use was later approved for corn. Aflatoxins are synthesized by a gene cluster consisting of approximately 25 genes (Yu et al., Applied and Environmental Microbiology, Volume 70, 1253-1262, 2004). Cyclopiazonic acid (CPA), an unrelated mycotoxin produced by *A. flavus*, is synthesized by a gene cluster adjacent to the aflatoxin gene cluster (Chang et al., Fungal Genetics and Biology, Volume 46, 176-182, 2009). Nonproduction of aflatoxins in AF36 is due to a single nucleotide polymorphism in the polyketide synthase gene early in the aflatoxin pathway (Ehrlich and Cotty, Applied Microbiology and Biotechnology, Volume 65, 473-478, 2004), whereas NRRL 21882 is missing the entire aflatoxin and CPA gene clusters (Chang et. al., Fungal Genetics and Biology, Volume 42, 914-923, 2005; Chang et al., 2009, supra). Other *A. flavus* strains that do not produce aflatoxins contain various nucleotide polymorphisms and partial deletions in the aflatoxin gene cluster (Chang et al., 2005, supra; Donner et al., Food Additives and Contaminants, Volume 27, 576-590, 2010).

Fungal vegetative compatibility, or the ability of strains to form stable hyphal fusions with each other, is controlled by a series of het loci whose genes must all be identical for stable fusions to occur (Leslie, Annual Review of Phytopathology, Volume 31, 127-150, 1993). Populations are often divided into subpopulations called vegetative compatibility groups (VCGs) consisting, of vegetatively compatible individuals. Because the het loci are scattered throughout the genome, VCGs provide an effective multilocus measure of genetic diversity within populations. In *A. flavus* populations, strains vary greatly in their capacity to produce aflatoxins and CPA, and most of this variation can be attributed to differences among VCGs (Horn et al., Mycologia, Volume 88, 574-587, 1996). The non-aflatoxin-producing component of *A. flavus* populations also exhibits high genetic diversity based on the large number of VCGs (Horn and Dorner, Applied and Environmental Microbiology, Volume 65, 1444-1449, 1999).

Cotty (U.S. Pat. No. 5,171,686, issued Dec. 15, 1992 and U.S. Pat. No. 5,294,442, issued Mar. 15, 1994) discloses a non-toxigenic strain of *A. flavus* which inhibits aflatoxin production by toxigenic strains. The patent teaches that agricultural commodities inoculated simultaneously with both a non-toxigenic strain and a toxigenic strain produce seed with up to 100-fold less aflatoxin than commodities inoculated with a toxigenic strain alone. The patent only discloses that the patented strain fails to produce aflatoxin. There is no disclosure of its lack of ability to produce other toxins such as, for example, CPA.

Cole et al. (U.S. Pat. No. 5,297,661, issued Mar. 8, 1994) and Dorner et al. (Journal of Food Protection, Volume 55, 888-892, 1992) disclose a non-aflatoxigenic strain of *A. parasiticus*. The references teach the use of this strain as a biocontrol agent which reduces aflatoxin contamination of soil-borne crops.

Phildain et. al. (International Journal of Food Microbiology, Volume-93, 31-40, 2004), Takahashi et al. (Journal of Food Protection, Volume 67, 90-95, 2004), Tran-Dinh et al. (Mycological Research, Volume 103, 1485-1490, 1999), and Wei and Jong (Mycopaihologia, Volume 93, 19-24, 1986) all disclose non-toxigenic strains of *A. flavus* wherein the strains do not produce aflatoxin.

Horn et al. (1996, supra) and Horn and Dorner (1999; supra) disclose isolates of *A. flavus* that fail to produce the mycotoxins aflatoxin and CPA.

While various strains of non-toxigenic *Aspergillus* for control of toxigenic fungi are known in the art, there still remains a need for effective biocontrol agents for toxigenic fungi. The present invention described below includes non-toxigenic strains of *Aspergillus*, especially non-toxigenic strains of *A. flavus*, which are antagonistic to toxigenic fungi. The present invention also provides a method for controlling toxigenic fungi in agricultural crops which is different from the related art methods.

SUMMARY OF THE INVENTION

It is therefore an object of the present invention to provide biocontrol agents for the control of toxigenic fungi in plants.

Another object of the present invention is to provide non-toxigenic fungi which are biocontrol agents for at least reducing contamination of crops with toxin-producing fungi.

It is another object of the present invention to provide non-toxigenic strains of *A. flavus* as biocontrol agents for at least reducing contamination of crops with toxin-producing fungi.

A further object of the present invention is to provide an agricultural biocontrol composition containing at least one non-toxigenic strain of *Aspergillus flavus*.

Another object of the present invention is to provide a method for biocontrol of toxin-producing fungi in plants which includes applying at least one non-toxigenic strain of fungi to the soil or by aerial dispersion.

A further object of the present invention is to provide a biocontrol method for peanuts, corn, cotton and tree nuts, which includes applying at least one non-toxigenic strain of *A. flavus* to the soil.

Further objects and advantages of the present invention will become apparent from the following description.

Deposit of the Microorganisms

*Aspergillus flavus* strains of the present invention are designated NRRL 50427, NRRL 50428, NRRL 50429, NRRL 50430, and NRRL 50431. They were deposited on 26 Oct. 2010. They were deposited under the provisions of the Budapest Treaty, on the International Recognition of the Deposit of Microorganisms for the Purposes of Patent Procedure and the Regulations there under (Budapest Treaty) with the U.S.D.A., Agricultural Research Service Patent Culture Collection, National Center for Agricultural Utilization Research, 1815 N. University Street, Peoria, Ill. 61604. Access to this deposit will be available during the pendency of the application to the Commissioner of Patents and Trademarks and persons determined by the Commissioner to be entitled thereto upon request under 37 C.F.R. 1.14 and 35 U.S.C. 122. The deposits are available as required by foreign patent laws in countries where counterparts of the subject application, or it progeny are filed. However, it is to be understood that the availability of a deposit does not constitute a license to practice the subject invention in derogation of patent rights granted by a government action. Upon allowance of any claims in the application, the Applicant(s) will maintain and will make this deposit available to the public pursuant to the Budapest Treaty.

DETAILED DESCRIPTION OF THE INVENTION

The addition of highly competitive, non-toxigenic-strains of *A. flavus* as well as mixtures of any of the strains to soil or to plants results in at least lower concentrations of toxins in agricultural commodities. The non-toxigenic strains of *Aspergillus* become biocompetitive with the soil microflora and prevent buildup of toxin-producing strains that normally occur during late-season drought. Through biocompetition, non-toxigenic strains added to the soil greatly outnumber toxigenic strains of fungi found naturally in soil. Therefore, any crop subjected to late-season drought stress is invaded predominantly by the biocompetitive strains which are unable to produce toxins.

For purposes of this invention, a fungal preparation or fungal agricultural biocontrol composition refers to a microbial preparation wherein the microbes comprise, consists essentially of, or consists of non-toxigenic strains of *Aspergillus flavus* and an agriculturally acceptable carrier. The fungal preparations may contain one or more non-toxigenic strains of *Aspergillus flavus*. Non-toxigenic strains of *Aspergillus flavus* include any strain which does not produce the toxins aflatoxin and cyclopiazonic acid. The agricultural biocontrol composition for purposes of this invention includes a non-toxigenic strain or strains of fungus in an agriculturally acceptable carrier which may be any carrier which the fungi can be added to or attached to and is not harmful to the fungi or crops which are treated with the composition. Non-limiting examples of non-toxigenic strains include *Aspergillus*, especially *A. flavus*. The fungi especially useful in the present invention are: NRRL-50427, NRRL 50428, NRRL 50429, NRRL 50430, and NRRL 50431.

Non-toxigenic strains of *Aspergillus flavus* are formulated as single strains on granular food sources, such as, for example, hulled barley or rice. The fungal conidia are suspended in an oil such as, for example, mineral oil or vegetable oil, and then coated onto the granular food source to form a granular food source mixture. Diatomaceous earth is then added to the granular food source mixture to create a free-flowing formulation. These food sources contain approximately $10^5$-$10^6$ colony forming units (CFU) of fungi per gram of food source.

The non-toxigenic strains of *Aspergillus* are applied to soil or to plants by aerial dispersion in amounts effective to at least reduce toxin levels in agricultural commodities. As used herein "to at least reduce toxin levels" refers to a reduction in amounts of toxin as compared to that which would be expected in agricultural commodities which were not treated according to methods of the present invention. Any accurate method for measuring and comparing toxin levels may be used for such comparisons, as would be apparent to those skilled in the art. As used herein "in amounts effective" or "an effective amount" refers to the amount of the fungal formulation administered wherein the effect of the administration acts to reduce toxin contamination of agricultural commodities. The granular product is applied over the developing crop at a rate of approximately 10 to 20 pounds-per acre. The strains can be applied as single strain compositions or can be mixed in about equal proportions to provide a composition made up of different non-toxigenic strains of *Aspergillus*.

The following examples are intended only to further illustrate the invention and are not intended to limit the scope of the invention as defined by the claims. Individual peanut seeds were used to exemplify the invention and to evaluate the ability of different non-toxigenic *A. flavus* strains to inhibit aflatoxin-production by aflatoxigenic strains because seeds of most plants infected with aflatoxignic strains represent the unit applicable to infection in the field.

EXAMPLE 1

The non-toxigenic strains of *Aspergillus* were isolated from agricultural soils in the United States (Horn and Dorner, Mycologia, Volume 90, 767-776, 1998) (Table 1). Strain NRRL 21882 is the active ingredient in the biocontrol formulation AFLA-GUARD® which is described in U.S. Pat. No. 6,306,386 issued Oct. 23, 2001. The inability of the strains in Table 1 to produce aflatoxins and CPA and their VCG designations were previously determined (Horn and Dorner, 1999, supra); aflatoxin gene cluster deletion groups are based on Chang et al. (2005, supra). The eight aflatoxigenic strains were obtained from soil in a single peanut field in Georgia, USA (Horn and Greene, Mycologia, Volume 87, 324-332, 1995). VCGs and aflatoxin/CPA production for aflatoxigenic strains were reported by Horn and Greene (1995, supra) and Horn et al. (1996, supra), respectively.

Nitrate nonutilizing mutants (niaD) of all the *Aspergillus flavus* strains were used in experiments so that strains could be easily identified when examining fungal sporulation on seeds. NiaD mutants for inoculating seeds and cnx mutants for identifying the niaD strains through complementation were created on a chlorate medium and identified by growth on different nitrogen sources according to Horn and Greene (1995, supra). Wild-type strains and their niaD mutants of non-toxigenic *A. flavus* were previously shown to be equally effective in reducing aflatoxins in cotton and peanut seeds (Cotty and Bayman, Phytopathology, Volume 83, 1283-1287, 1993; Horn and Dorner, Biocontrol Science and Technology, Volume 19, 249-262, 2009). The strains were maintained on Czapek agar slants and as dry conidia on silica gel.

EXAMPLE 2

Inoculum was prepared by growing *A. flavus* niaD strains (approximately 14 days; approximately 30 degrees C.) on slants of ammonium medium (Horn and Greene, 1995, supra) modified with approximately 400 g/L sucrose to stimulate sporulation. Conidia from slant cultures were suspended in approximately 10 mL sterile water containing approximately 50 µL/L Tween 20 and adjusted to approximately $2 \times 10^6$ conidia/mL. Approximately 1 mL of each non-toxigenic strain was combined with approximately 1 mL of an aflatoxigenic strain or approximately 1 mL water for controls with single non-toxigenic and aflatoxigenic strains, giving a final concentration of approximately $10^6$ conidia/mL per strain. Wounds on peanut seeds were inoculated with approximately 1 µL of each conidial mixture using a micro volume pipette for approximately 1000 conidia per strain.

Viable fungus-free peanut seeds (cultivar Georgia Green) were prepared according to Horn (Mycologia, Volume 97, 202-217, 2005). Briefly, peanut pods were surface sterilized and seeds were aseptically removed and incubated in a desiccator jar for approximately 7 days at approximately 37 degrees C. containing NaCl solution at a water activity of approximately 0.96. Seeds were then examined microscopically for fungal growth, and the fungus-free seeds were wounded at the center of one cotyledon with a sterile cork borer. Seeds were glued to the bottom of partitioned plates with the wound upright. Wounds were inoculated with conidial mixtures, and the seeds Were incubated at the same water activity for an additional 7 days at approximately 30 degrees-C. Each combination of non-toxigenic and aflatoxigenic strains was inoculated onto approximately 20 seeds (approximately 4 seeds/plate). Experiments consisted of one aflatoxigenic strain alone as a control (approximately 20 seeds) and the same aflatoxigenic strain paired with eight non-toxigenic strains (approximately 8×20=approximately 160 seeds); all experiments were performed twice. The eight non-toxigenic strains were each examined alone on approximately 20 seeds in two replicate experiments.

Sporulation by non-toxigenic and/or aflatoxigenic *A. flavus* niaD strains was examined at each end of the peanut seed following seed colonization to assess strain dominance. Conidia were removed with a transfer needle from the hilar end of the seed, which also contained the embryo, and from the opposite end without the hilum. Sporulation typically occurred at the extreme ends of the seeds; in instances where colony growth was more restricted, conidia Were removed from colony edges aligned with the seed ends. Conidia were transferred to vials containing approximately 0.5 mL of approximately 0.2% water agar with Tween 20. *A. flavus* niaD strains were identified through the formation of heterokaryons when paired with complementary cnx mutants on Czapek agar plates containing nitrate as a sole nitrogen source (Horn and Greene, 1995, supra). Plates were single-point inoculated with the seed conidial suspension from one end of the seed and the two cnx mutants representing the non-toxigenic and aflatoxigenic strains used to inoculate the seed; the three inoculation points were separated from each other at the center of the plate by approximately 5 mm. Aflatoxins were extracted from individual seeds with methanol and were quantified using high performance liquid chromatography according to Horn and Dorner (2009, supra).

The effect of *A. flavus* strains on aflatoxin $B_1$ concentration (ppm) in seeds was examined as a nonparametric two-way ANOVA on ranks with a nested design, with non-toxigeniic and aflatoxigenic strains as variates and with experiment as a component of the nested design. Within each experiment, aflatoxin $B_1$ Values were compared using a Kruskal-Wallis one-way ANOVA on ranks followed by the Tukey Test for multiple comparison of ranks. Sporulation ratings were based on the presence of non-toxigenic strains at either end of the seed (0=non-toxigenic strain not detected at either end; 1=non-toxigenic strain detected at one end; 2=non-toxigenic strain detected at both ends); these raw data were not examined statistically because of the large number of ties.

Pearson Product Moment correlations were performed between experiments 1 and 2 for mean aflatoxin $B_1$ concentrations and for mean sporulation ratings. Correlations also were examined between mean aflatoxin $B_1$ concentrations and mean seed sporulation ratings within each experiment and for all experiments combined. Mann-Whitney Rank Sum Test was used to compare aflatoxin $B_1$ concentrations in seeds inoculated with wild-type NRRL-29473 alone and concentrations in seeds inoculated with wild-type non-toxigenic-NRRL 35739+wild-type aflatoxigenic NRRL 29473. SAS statistical package version 9.2 (SAS Institute, Cary, N.C.) was used to perform the two-way ANOVA (GLM Procedure) and to calculate percentages of variance components (NESTED Procedure); all other statistical tests were performed with SigmaStat version 3.5 (Jandel Scientific, San Rafael, Calif.).

Eight non-toxigenic *A. flavus* strains varying in their VCG designation and aflatoxin gene cluster deletion pattern (Table 1) were tested for their ability to inhibit aflatoxin $B_1$ production on individual peanut seeds when co-inoculated with eight aflatoxin-producing strains also belonging to different VCGs. A two-way ANOVA (Table 2) based on separate aflatoxin analyses of approximately 2559 seeds indicated that there was a significant non-toxigenic x aflatoxigenic strain interaction ($F_{49,64}$=1.97; P=0.0055; this interaction factor accounted for approximately 15.4% of the variance. Factors for non-toxigenic strain, aflatoxigenic strain and experiment accounted for approximately 25.3, 40.1, and 19.2% of the variance, respectively. To further examine the variation attributed to experiments, correlation analyses between replicate experiments (Table 3) were performed on mean aflatoxin values (n=8). Experiments 1 and 2 values were positively correlated for NRRL 29459, 29497, and 29473 (P<0.0001; $R^2$=0.97-0.99) but not for NRRL 29499, 29501, 29478, 29466, and 29488 (P>0.05; $R^2$=0.08-0.44).

Non-toxigenic strains overall lowered aflatoxin $B_1$ production by the aflatoxigenic strains (Table 3), though not all co-inoculated seeds were significantly different from the controls (aflatoxigenic strains alone) due to the high level of variation among individual seeds. Experiments with seeds inoculated with the eight non-toxigenic strains alone showed mean aflatoxin $B_1$ values≤0.001 ppm. In a majority of cases, reduction of aflatoxin $B_1$ in co-inoculated seeds was considerably greater than the expected 50% based on a 50:50 mixture of conidia as inoculum (Table 3). Non-toxigenic NRRL 35739 was an exception, with co-inoculations typically resulting in no significant reduction in aflatoxin $B_1$. Co-inoculation of NRRL 35739 and aflatoxigenic NRRL 29473 (experiment 1) even resulted in a significant increase in aflatoxin $B_1$ (Table 3). To ensure that the niaD mutation was not associated with the increased aflatoxin production, wild-type strains of both non-toxigenic NRRL 35739 and aflatoxigenic NRRL 29473 were co-inoculated onto peanut seeds. Mean aflatoxin $B_1$ concentrations in seeds (n=20) were approximately 3.70±5.84 ppm (±SD) for NRRL 29473 alone and approximately 19.69±21.70 ppm for NRRL 35.739+NRRL 29473. The two treatments were significantly different (P=0.001) according to Mann-Whitney Rank Sum Test ($U_s$=322.00).

The effectiveness of non-toxigenic strains in reducing aflatoxin production by aflatoxigenic strains was assessed according to the number of experiments (i=16) in which aflatoxin concentrations were most significantly different from the control (aflatoxigenic strain alone) (Table 3). Non-toxigenic strains were ranked as follow: NRRL 50427=16 experiments, NRRL 50428=16, NRRL 50429=12, NRRL 50430=12, NRRL 50431=10, NRRL 62099=8, NRRL 21882=3, and NRRL 35739=0.

All correlations between experiments 1 and 2 involving mean non-toxigenic sporulation ratings were statistically significant (P<0.05; $R^2$=0.63-0.89; n=8), with the exception of NRRL 29488, which was barely nonsignificant (P=0.07; $R^2$=0.44). Correlations between mean aflatoxin $B_1$ concentrations and mean seed sporulation ratings were not significant for each of the 16 experiments (P>0.05; $R^2$=0.00005-0.27; n=8) or for all experiments combined into one data set (P=0.85; $R^2$=0.0003; n=128).

A large proportion (approximately 98 of 128) of mean sporulation ratings for co-inoculated seeds were <1.00 (Table 4), indicating that sporulation was often dominated by the aflatoxigenic strains. Sporulation on peanut seeds by non-toxigenic strains was assessed by the number of experiments (n=16) in which the mean-sporulation rating was ≥1.00 (Table 4). Non-toxigenic strains were ranked as follows: NRRL 50428=11 experiments, NRRL 62099=10, NRRL 35739=5, NRRL 50427=3, NRRL 50431=2, NRRL 50429=1, NRRL 50430=1, and NRRL 21882=0. Rankings of non-toxigenic strains based on sporulation rating did not correspond to rankings based on aflatoxin $B_1$ reduction.

TABLE 1

Characteristics of *A. flavus* strains used in experiments.[1]

| Culture number[2] | | Aflatoxin $B_1$ | CPA | VCG | Aflatoxin gene cluster deletion group |
|---|---|---|---|---|---|
| NRRL | NPL | | | | |
| 50427 | AL4-7 | − | − | 64 | H |
| 50428 | NC7-8 | − | − | 79 | F |
| 50429 | TX21-5 | − | − | 71 | E |
| 50430 | AL4-3 | − | − | 70 | H |
| 50431 | SC5-1 | − | − | 67 | H |
| 62099 | AL6-8 | − | − | 77 | A |
| 35739 | TX13-5 | − | − | 76 | E |
| 21882[3] | | − | − | 24 | H |
| 29499 | | + | + | 28 | |
| 29501 | | + | + | 29 | |
| 29459 | | + | + | 6 | |
| 29497 | | + | + | 27 | |
| 29478 | | + | + | 23 | |
| 29473 | | + | + | 17 | |
| 29466 | | + | + | 14 | |
| 29488 | | + | + | 25 | |

[1]Strain characteristics obtained from the following: aflatoxin $B_1$ and cyclopiazonic acid (CPA) production (Horn et al., 1996, supra; Horn and Dorner, 1999, supra); vegetative compatibility group (VCG) (Horn and Greene, 1995, supra; Horn and Dorner, 1999, supra); and aflatoxin gene cluster deletion group (Chang et al., 2005, supra).

[2]Culture collection designations: NRRL (Agricultural Research Service Culture Collection, Peoria, IL, USA) and NPL (National Peanut Research Laboratory, ARS, USDA, Dawson, GA, USA). Two-letter designations in NPL numbers indicate the state from which the strain originated in the United States.

[3]Non-toxigenic *A. flavus* strain used in the biocontrol formulation AFLA-GUARD ®.

TABLE 2

Two-way ANOVA on ranks with nested design for aflatoxin $B_1$ (ppm) in peanut seeds (n = 2559).

| Source of variation | DF | Sum of squares | Mean square | F value | P |
|---|---|---|---|---|---|
| Non-toxigenic strain | 7 | 65914233.35 | 9416319.05 | 24.10 | <0.0001 |
| Aflatoxigenic strain | 7 | 91635997.84 | 13090856.83 | 33.50 | <0.0001 |
| Non-toxigenic × Aflatoxigenic strain | 49 | 37763609.71 | 770685.91 | 1.97 | 0.0055 |
| Experiment (Non-toxigenic × Aflatoxigenic strain) (Error) | 64 | 25006662.71 | 390729.10 | | |

TABLE 3

Aflatoxin $B_1$ production (ppm) by *A. flavus* in single peanut seeds when coinoculated with non-toxigenic strains.[1]
Aflatoxigenic strain[2]

| | NRRL 29499 | | NRRL 29501 | | NRRL 29459 | | NRRL 29497 | |
|---|---|---|---|---|---|---|---|---|
| | Exp 1 | Exp 2 | Exp 1 | Exp 2 | Exp 1 | Exp 2 | Exp 1 | Exp 2 |
| Control[3] | 28.61 a | 47.80 a | 21.07 a | 31.80 a | 18.80 a | 36.88a | 30.58 a | 39.25 ab |
| | | | NRRL Non-toxigenic strain[2] | | | | | |
| 50427 | 2.23 bcd | 3.84 de | 0.39 d | 0.21 de | 0.02 c | 0.29 e | 2.06 cd | 0.20 e |
| 50428 | 0.49 d | 1.42 e | 1.81 cd | 0.05 e | 0.05 c | 0.75 cde | 1.05 d | 0.35 de |

TABLE 3-continued

Aflatoxin B$_1$ production (ppm) by *A. flavus* in single peanut seeds when coinoculated with non-toxigenic strains.[1]
Aflatoxigenic strain[2]

| | | | | | | | | |
|---|---|---|---|---|---|---|---|---|
| 50429 | 3.01 bcd | 17.47 abcd | 4.46 bc | 3.53 bcd | 0.08 c | 0.27 e | 1.89 cd | 1.41 cde |
| 50430 | 5.09 bc | 4.62 bcde | 10.58 ab | 0.26 cde | 0.25 bc | 0.54 de | 4.68 bc | 0.35 de |
| 50431 | 2.78 cd | 4.71 cde | 5.81 bc | 0.71 bcde | 2.24 ab | 2.95 bcd | 9.03 ab | 4.54 abc |
| 62099 | 5.91 ab | 11.03 abc | 3.53 bc | 1.04 bcd | 0.05 c | 0.43 cde | 0.65 d | 0.15 e |
| 21882[4] | 9.46 bc | 15.72 ab | 4.43 bc | 3.30 ab | 0.90 ab | 3.95 abc | 7.9 abc | 2.39 bcd |
| 35739 | 9.09 abc | 13.87 abcd | 11.59 ab | 6.08 bc | 18.56 a | 23.23 ab | 43.27 a | 78.75 a |

| | NRRL 29478 | | NRRL 29473 | | NRRL 29466 | | NRRL 29488 | |
|---|---|---|---|---|---|---|---|---|
| | Exp 1 | Exp 2 | Exp 1 | Exp 2 | Exp 1 | Exp 2 | Exp 1 | Exp 2 |
| Control | 25.72 a | 48.07 a | 22.98 b | 29.62 ab | 1.87 a | 7.32 a | 26.69 a | 18.41a |

NRRL Non-toxigenic strain[2]

| | | | | | | | | |
|---|---|---|---|---|---|---|---|---|
| 50427 | 0.62 e | 0.27 c | 1.27 c | 1.03 f | 0.04 bcd | 0.13 cd | 0.77 d | 1.31 b |
| 50428 | 0.39 e | 0.73 c | 1.52 bc | 3.13 cdef | 0.02 cd | 0.06 bcd | 0.99 d | 2.38 b |
| 50429 | 1.76 de | 1.18 bc | 5.16 bc | 5.51 cde | 0.06 bcd | 0.11 bcd | 1.97 d | 0.92 b |
| 50430 | 2.35 bcde | 1.15 bc | 3.11 bc | 1.33 ef | 0.05 bcd | 0.18 bc | 1.93 cd | 2.94 b |
| 40431 | 1.74 cde | 0.36 c | 5.47 bc | 7.27 bcd | 0.01 d | 0.02 d | 2.09 cd | 1.09 b |
| 62099 | 6.04 abc | 13.10 a | 1.57 bc | 1.89 def | 0.08 ab | 0.13 bc | 3.26 bcd | 1.43 b |
| 21882[4] | 6.58 bcd | 1.29 bc | 4.47 b | 8.43 bc | 0.11 bc | 0.12 bcd | 11.61 ab | 2.26 b |
| 35739 | 7.81 ab | 6.60 ab | 102.91 a | 67.23 a | 0.08 bc | 0.28 ab | 10.78 abc | 19.36 a |

[1]Statistics were performed using Kruskal-Wallis one-way ANOVA on ranks following by the Tukey test for multiple comparison of ranks. Means (n = 20 seeds) are shown for replicate experiments 1 and 2; however, significant differences are based on ranking of variates rather than on means.
Values not sharing a common letter within a column are significantly different (P ≤ 0.05). Numbers in bold represent values most significantly different from the control (aflatoxigenic strain alone) but not significantly different from each other.
[2]Culture collection designations: NRRL (Agricultural Research Service Culture Collection, Peoria, IL, USA) and NPL (National Peanut Research Laboratory, ARS, USDA, Dawson, GA, USA).
[3]Seeds inoculated with aflatoxigenic strain alone.
[4]Active ingredient of the biocontrol formulation AFLA-GUARD ®.

TABLE 4

Sporulation by non-toxigenic strains on single peanut seeds when coinoculated with aflatoxigenic strains.[1]
Aflatoxigenic strain[2]

| NRRL Non-toxigenic | NRRL 29499 | | NRRL 29501 | | NRRL 29459 | | NRRL 29497 | |
|---|---|---|---|---|---|---|---|---|
| Strain[2] | Exp 1 | Exp 2 | Exp 1 | Exp 2 | Exp 1 | Exp 2 | Exp 1 | Exp 2 |
| 50427 | 0.65 | 1.15 | 0.70 | 0.50 | 1.00 | 0.95 | 0.00 | 0.50 |
| 50428 | 1.35 | 1.45 | 1.20 | 1.65 | 1.55 | 1.45 | 0.40 | 0.85 |
| 50429 | 0.65 | 0.65 | 0.40 | 0.30 | 0.70 | 1.05 | 0.30 | 0.50 |
| 50430 | 0.25 | 0.55 | 0.15 | 0.60 | 0.50 | 0.75 | 0.00 | 0.65 |
| 50431 | 0.65 | 0.95 | 0.40 | 0.45 | 1.25 | 1.10 | 0.00 | 0.05 |
| 62099 | 1.90 | 1.70 | 0.65 | 0.75 | 2.00 | 1.80 | 1.00 | 1.25 |
| 21882[3] | 0.00 | 0.10 | 0.20 | 0.20 | 0.60 | 0.60 | 0.00 | 0.05 |
| 35739 | 0.50 | 0.70 | 0.65 | 0.85 | 1.85 | 1.35 | 0.55 | 0.70 |

| NRRL Non-toxigenic | NRRL 29478 | | NRRL 29473 | | NRRL 29466 | | NRRL 29488 | |
|---|---|---|---|---|---|---|---|---|
| Strain[2] | Exp 1 | Exp 2 | Exp 1 | Exp 2 | Exp 1 | Exp 2 | Exp 1 | Exp 2 |
| 50427 | 0.30 | 0.10 | 1.10 | 0.05 | 0.00 | 0.10 | 0.85 | 0.15 |
| 50428 | 1.85 | 1.40 | 1.50 | 0.90 | 0.20 | 0.70 | 1.25 | 1.15 |
| 50429 | 0.05 | 0.50 | 0.25 | 0.00 | 0.00 | 0.60 | 0.00 | 0.65 |
| 50430 | 0.00 | 0.05 | 0.05 | 0.20 | 0.00 | 0.25 | 0.55 | 0.40 |
| 50431 | 0.00 | 0.20 | 0.30 | 0.05 | 0.10 | 0.20 | 0.70 | 0.30 |
| 62099 | 1.40 | 0.65 | 1.75 | 0.70 | 0.60 | 0.75 | 1.15 | 1.35 |
| 21882[3] | 0.05 | 0.00 | 0.05 | 0.05 | 0.00 | 0.05 | 0.65 | 0.60 |
| 35739 | 1.00 | 0.75 | 0.70 | 0.40 | 1.65 | 1.20 | 0.75 | 0.05 |

[1]Means (n = 20 seeds) shown for replicate experiments 1 and 2. Sporulation was quantified according to the presence of the non-toxigenic strain at the basal and/or apical end of the peanut seed: 0 = non-toxigenic strain not detected at either end; 1 = non-toxigenic strain detected at one end; 2 = non-toxigenic strain detected at both ends. Numbers in bold (≥1.00) represent an equal or greater dominance of the non-toxigenic strain on the peanut seed.
[2]Culture collection designations: NRRL (Agricultural Research Service Culture Collection, Peoria, III, USA) and NPL (National Peanut Research Laboratory, ARS, USDA, Dawson, GA, USA)
[3]Non-toxigenic *A. flavus* strain used in the biocontrol formulation AFLA-GUARD ®

All publications and patents mentioned in this specification are herein incorporated by reference to the same extent as if each individual publication or patent was specifically and individually indicated to be incorporated by reference.

The foregoing detailed description is for the purpose of illustration. Such detail is solely for that purpose and those skilled in the art can make variations therein without departing from the spirit and scope of the invention.

We claim:

1. A non-toxigenic fungal biocontrol agent comprising a biologically pure *Aspergillus* strain selected from the group consisting of NRRL 50427, NRRL 50429, NRRL 50430, NRRL 50431 and mixtures thereof; wherein said strain does not produce aflatoxin and cyclopiazonic acid.

2. An agricultural biocontrol composition comprising an agriculturally acceptable carrier and a biologically pure non-toxigenic strain of *Aspergillus* selected from the group consisting of NRRL 50427, NRRL 50429, NRRL 50430, NRRL 50431, and mixtures thereof; wherein said strain does not produce aflatoxin and cyclopiazonic acid.

3. A method for reducing toxin contamination of agricultural commodities comprising applying the agricultural biocontrol composition comprising an agriculturally acceptable carrier and one more biologically pure, non-toxigenic strains of *Aspergillus* selected from the group consisting of NNRL 50427, NRRL 50429,NRRL 50430, NRRL 50431 and mixtures thereof; wherein said one or more strains do not produce aflatoxin and cyclopiazonic acid.

4. The method of claim 3 wherein said agricultural commodities are selected from the group consisting of peanuts, corn, cotton, and tree nuts.

5. A method for reducing aflatoxin contamination of an agricultural commodity comprising applying to said agricultural commodity one or more biologically pure, non-toxigenic strains of *Aspergillus* selected from the group consisting of NRRL 50427, NRRL 50429, NRRL 50430, NRRL 50431 and mixtures thereof; wherein said one or more strains of *Aspergillus* do not produce aflatoxin and cyclopiazonic acid.

6. The method of claim 5 wherein said agricultural commodity is selected from the group consisting of peanut, corn, cotton, and tree nut.

\* \* \* \* \*